United States Patent [19]

Blum

[11] Patent Number: 4,894,463
[45] Date of Patent: Jan. 16, 1990

[54] PROCESS FOR PREPARING THIOPHENE DERIVATIVES

[76] Inventor: Holger Blum, Parkalee 75, 2000 Hamburg 13, Fed. Rep. of Germany

[21] Appl. No.: 232,678

[22] Filed: Aug. 16, 1988

[30] Foreign Application Priority Data

Aug. 17, 1987 [DE] Fed. Rep. of Germany ....... 3727428
Sep. 15, 1987 [EP] European Pat. Off. ......... 87113493.8

[51] Int. Cl.$^4$ .......................................... C07D 235/00
[52] U.S. Cl. ................................................... 548/303
[58] Field of Search ........................................ 548/303

[56] References Cited

U.S. PATENT DOCUMENTS 4,044,020 8/1977 Marx et al. ........................... 548/303
4,782,165 11/1988 Sklavounos .......................... 548/303

Primary Examiner—Mary C. Lee
Assistant Examiner—Richard A. Sharpe
Attorney, Agent, or Firm—Fleit, Jacobson, Cohn, Price, Holman & Stern

[57] ABSTRACT

Thiophene derivatives of the general formula

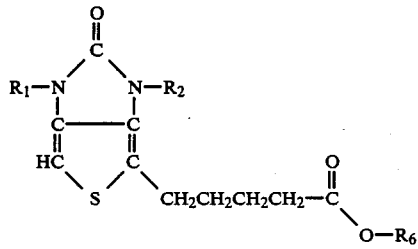

wherein $R_1$ and $R_2$, which may be the same or different, each are hydrogen or lower acyl and $R_6$ is hydrogen or lower alkyl, are prepared by the reaction of a compound of the general formula

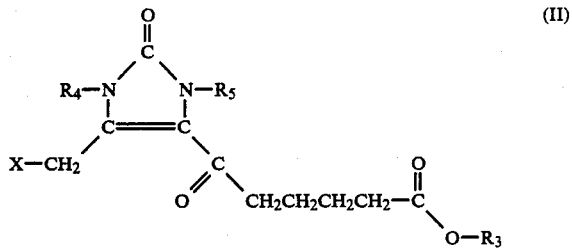

wherein $R_3$ is lower alkyl, $R_4$ and $R_5$ are lower acyl and X is chlorine, bromine or iodine, with a strong basic quaternary ammonium anion exchange resin in the monothiophosphate form to form a polymer intermediate product of the formula

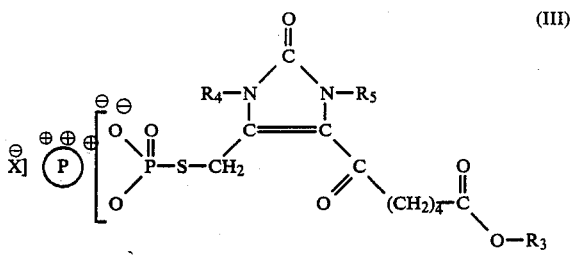

wherein $R_3$, $R_4$, and $R_5$ have the significances given above, and (P)+++ represents a polymer cation, which after purification in an acidic medium is reacted to the thiophene derivative of formula (I).

The invention further relates to the novel polymer compound of formula (III) obtained in this process as an intermediate product.

4 Claims, No Drawings

PROCESS FOR PREPARING THIOPHENE DERIVATIVES

BACKGROUND OF THE INVENTION

Thiophene derivatives of formula (I), which is set forth below, may be converted into the vitamin (±)-biotin by hydrogenation under suitable conditions. Suitable conditions for the catalytic hydrogenation are described in "Helvetica Chimica Acta", 59 (1976), page 1 005, as well as in DE-OS 30 18 109.

Further, it is known to react compounds of the formula (II), which is set forth below, with thioacetic acid, thiourea, thiourea acyl compounds or with sodium thiosulphate, to form S-containing intermediate products of the formula

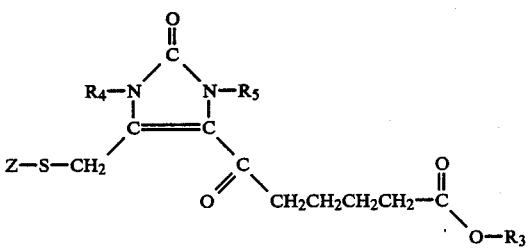

IV wherein $R_3$ is lower alkyl, $R_4$ and $R_5$ are lower acyl and Z is one of the residues described below.

The said S-containing intermediate products of formula IV, where $Z=CH_3CO-$ (thioacetate), may be prepared according to a process described by Taguchi et al in "Chemistry Letters" (1974), pages 729 to 730. Intermediate products of formula (IV), where $Z=C(=NH)-NH_2\cdot HBr$ (thiourea), may also be prepared according to a process described by Isaka et al in "Yakugaku Zasshi", 88 (4) (1968), pages 422 to 427. Intermediate products of formula (IV), where $Z=C(=NH)-NHCOPh\cdot HBr$ (benzoylthiourea) and $Z=-SO_2-O-Na$ (thiosulphate), may be prepared, as described by Zavyalov et al in "Izvestia Akademia Nauk. SSSR Ser. Chim. (1980), pages 1 943 to 1 945. According to Taguchi et al. (cf. "Chemistry Letters" (1974), pages 729 to 730) the intermediate product of formula (IV), where $Z=CH_3CO-$, is first subjected to alkaline hydrolysis to form an intermediate product of formula IV, where $Z=H$, and thereafter to intramolecular cyclisation in a mineral acidic medium to form the thiophene derivative of formula (I). The isothiuronium salt prepared from Isaka et al. (cf. Yakugaku Zasshi, 88 (4) (1968), pages 422 to 427) is also first subjected to alkaline hydrolysis and thereafter to intramolecular cyclisation in a mineral acidic medium to the thiophene derivative of formula (I). The intermediate products of formula IV may be converted into thiophene derivatives of formula (I) in an acidic medium in one step by hydrolysis and intramolecular cyclisation (cf. Zavyalov et al in "Izvestia Akademia Nauk. SSSR Ser. Chim." (1980), pages 1 943 to 1 945, SSSR-patent 579 767 and PCT application WO 86/02069).

However, when re-working the above mentioned processes for the preparation of thiophene derivates of formula (I), it has been found that these processes are not suited for the technical production on a large scale, in particular for an industrial performance, since they have a number of severe disadvantages:

(1) The 1,3-diacyl-4-halomethyl-5-(5-alkoxycarbonylpentanoyl)-4-imidazole-2-one of formula (II) used as a starting product is prepared by halogenation of the compound of formula (V)

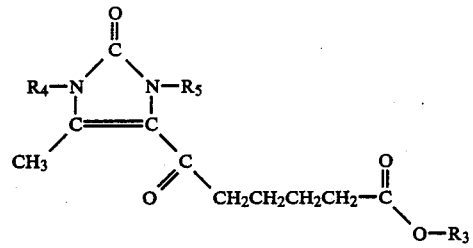

V wherein $R_3$, $R_4$ and $R_5$ have the significances given above (cf. Duschinsky and Dolan in "Am. Soc." 70 (1948), pages 657 to 662).

The crude halogenation product of formula (II) obtained thereby has to be brought to a high degree of purity by recrystallization before it can be reacted according to known processes. Without this prepurification, in the course of the subsequent chemical reaction by-products are formed, which are extremely difficult to separate and which result in an early poisoning of the noble metal catalysts in the catalytic hydrogenation of the thiophene derivatives of formula (I) obtained in a decrease of the yiled of (±)-biotin;

(2) The S-containing intermediate products of formula (IV) obtained according to known processes are unstable and decomposing compounds, which are not only difficult to handle on a technical scale but also are still in the need of an additional purification by recrystallization. According to the known processes the crude intermediate products of formula (IV) are obtained in the form of concentrates by evaporation of the reaction mixture. Generally, the impurities in such concentrates are decomposition products of the crude intermediate products or relatively low molecular substances. It The removal of such foreign substances from the concentrates for isolating the pure intermediate products of formula (IV) has turned out very difficult and rich in losses;

(3) In the known processes for preparing the thiophene derivatives of formula (I) it is necessary to use crystallization processes, which are extremely slow and time consuming in order to obtain pure products on a large technical scale. When the crystallization of the purified solutions obtained is carried out too rapidly, in frequent cases not a crystalline precipitate results, but first a cloudiness and then an oily precipitate, this making a further purification necessary, which in turn decreases the yield in crystalline end product considerably;

(4) Further, the known processes have the disadvantage that some lead to a low yield of 72% at most, and others are connected with difficulties upon application on a large technical scale, require the use of expensive solvents or do not allow direct crystallization.

SUMMARY OF THE INVENTION

It is one object of this invention to provide a process by which thiophene derivatives of the general formula (I), given below, which have sufficient purity for later hydrogenation, are produced in a technically simple and economical manner from a crude halogenation product having the general formula (II), which is set forth below.

It is another object of this invention to provide the vitamin (∓)-biotin by hydrogenation of the end product of the above process without prepurification of said end product.

In accordance with this invention there is provided an improved process for the preparation of thiophene derivatives, which have the general formula (I), given below, in which a compound having the general formula (II), given below, is reacted with a strong basic quaternary ammonium anion exchange resin in the monothiophosphate form.

In accordance with this invention there is also provided a new polymer, which occurs as an intermediate in the above process, and which has the general formula (III), given below.

It has now been found that this object can be met, when the synthesis of the thiophene derivatives of the formula (I) is carried out as described below.

DESCRIPTION OF PREFERRED EMBODIMENTS

In the invention described herein thiophene derivatives of the general formula

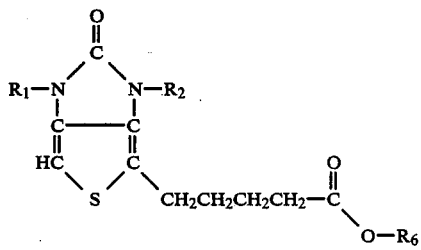

I wherein $R_1$ and $R_2$, which may be the same or different, each are hydrogen or lower acyl and $R_6$ is hydrogen or lower alkyl, are prepared. This process comprises the following steps:

(a) reacting a compound of the general formula

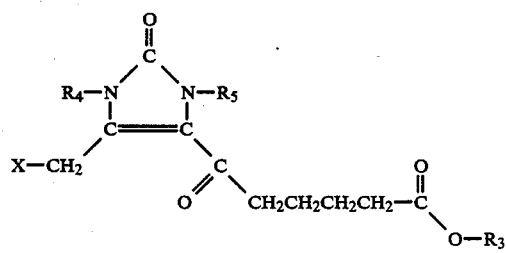

II wherein $R_2$ is lower alkyl, $R_4$ and $R_5$ are lower acyl and X is chlorine, bromine or iodine, with a strong basic quaternary ammonium anion exchange resin in the monothiophosphate form to form a polymer compound of the general formula

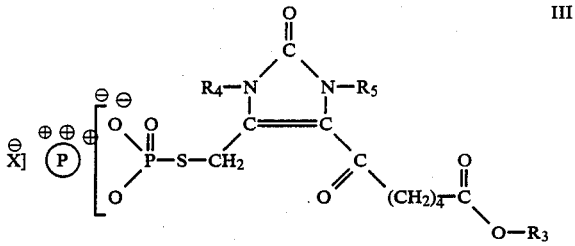

III wherein $R_3$, $R_4$ and $R_5$ have the significances given above and $(P)^{+++}$ represents a polymer cation, (b) separating the polymer intermediate product of the formula (III) obtained in step (a) from non-reacted accompanying substances by washing with a washing liquid capable of dissolving the accompanying substances, and then (c) reacting the washed polymer intermediate product of the formula (III) in an acidic medium to form the thiophene derivative of the formula (I),

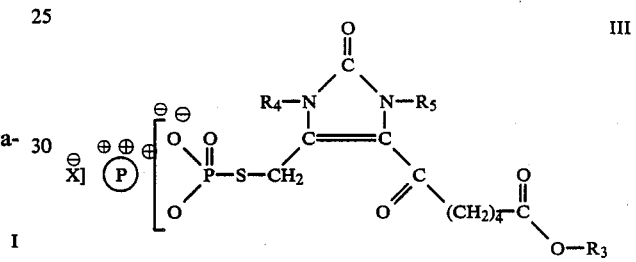

III wherein $R_3$ is lower alkyl and $R_4$ and $R_5$ are lower acyl.

The process of the invention for preparing the thiophene derivatives of the formula (I) and the new polymer compounds of the formula (III), which occur as intermediate products, is described in detail below.

When carrying out the process of the invention, first in step (a) a new polymer intermediate product of the formula (III) is prepared by reaction of a halogenated compound of the formula (II) with a strong basic quaternary ammonium anion exchange resin in the monothiophosphate form. Suitable strong basic quaternary ammonium anion exchange resins are known to the person skilled in the art (cf. K. Dorfner, "Ionenaustauscher", 3rd edition, De Gruyter, Berlin 1970).

For the preparation of the polymer intermediate products of the general formula (III) of the invention, different kinds of strong basic anion exchange resins may be used, such being preferred, which have a macroporous structure. Especially preferred are anion exchange resins, which have a macroporous structure and contain a polystyrene skeleton crosslinked with divinyl benzene, or consist of such skeleton. The quaternary ammonium groups may be bonded to the carrier by any divalent residue, e.g. an alkylene with preferably 1 to 4 carbon atoms, such as methylene. The nitrogen atom of the quaternary ammonium groups may have substituents, which may be the same or different, alkyl residues with 1 to 4 carbon atoms, especially methyl or ethyl, which may be substituted (e.g. by hydroxyl) being mentioned. As examples there are mentioned

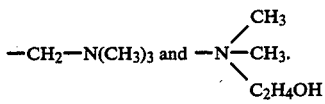

The anion exchangers usually are treated with chloride or acetate as counter ions and may be converted into the monothiophosphate form by treatment with an aqueous solution of alkali or alkaline earth metal salts of monothiophosphoric acid.

Methods and conditions, under which the anion exchange takes place, are known to the person skilled in the art. In a preferred procedure the anion exchanger is filled into the ion exchange column in the chloride or acetate form and is washed with water. Subsequently, an aqueous solution of alkali or alkaline earth metal salts of monothiophosphoric acid is passed through the column, either from the top or from the bottom, until the counter ions in the resin are completely exchanged and no chloride or acetate ions, respectively, are detected in the runoff liquid. Thereafter, the resin column is washed with water, until the runoff liquid is free from salt, and then the water in the resin bed is replaced by a suitable solvent.

Suitable solvents for the reaction of the crude halogenation product of formula (II) with the quaternary ammonium anion exchange resin in the monothiophosphate form are lower alkanols or mixtures of lower alkanols with inert aprotic solvents. Such suitable solvents may also contain low amounts of water, without adversely affecting the chemical reaction. It is of particular advantage to carry out the reaction in isopropanol as a solvent. According to another advantageous method, the reaction takes place in a mixture of a lower alkanol and dimethylformamide as solvents. The reaction of the dissolved crude halogenation product of formula (II) with the quaternary ammonium anion exchange resin in the monothiophosphate form generally takes place at temperatures from $-10°$ to $+30°$ C. The reaction time generally is 10 to 200, preferably 30 to 90 hours. The reaction is completed, when 95 to 99 mol percent of the halogenation product of formula (II) present in the solution are reacted with the anion exchange resin to the new polymer intermediate product of formula (III).

The progress of the reaction may be monitored by thin layer chromatographic (TLC) analysis of small samples. TLC generally was carried out on silica gel using pure ethyl acetate as eluent. The advantage of this reaction step of the invention is that a stable polymer intermediate product of formula (III) is obtained from the crude halogenation product of formula (II) and that at least two recrystallization steps and two evaporation steps may be dismissed.

The new polymer intermediate product of formula (III) obtained in step (a) has the physical properties of the anion exchange resin used and therefore is easy to handle. This advantage of the invention is made use of in the next process step (b) of the invention, when washing the new polymer intermediate product of formula (III) with solvents and thereby washing down accompanying substances and non-reacted halogenation product of the general formula (II).

It is of advantage to use polar solvents for this purification step. As such may be mentioned: lower alkanols, aprotic solvents, such as acetonitrile, dimethylformamide, dimethylsulfoxide, tetramethylenesulfone, dioxane, tetrahydrofurane and lower ketons. Further suitable solvents for washing down impurities from the new intermediate products of general formula (III) are lower aliphatic carboxylic acids, such as acetic acid and propionic acid. The washing step does not require technical skill and specific apparatuses, as the intermediate product of formula (III) is present in little plastic balls, which are easy to handle. The progress of the washing step may be monitored by known methods. A reliable method is the taking of samples from the washing solution. These samples are carefully evaporated. The remaining evaporation residue is a measure for the degree of washing.

The new polymer intermediate product of formula (III) purified by the washing in step (b) may now be converted into the thiophene derivative of general formula (I) in a manner known per se in an acidic medium by hydrolysis and cyclisation.

Upon hydrolysis, the P-S-bonding of the polymer intermediate product of formula (III) is cleaved, and the mercaptane of general formula (IV), wherein Z=H, forms.

As acids for this reaction medium may be exemplified: dilute mineral acids and strong organic acids, such as sulfonic acids. In particular, it has turned out advantageous for the performance of the process of the invention to use such acids for the production of the acidic medium, the acidic dissociation exponent pKs of which is $<3$, when measured in water. In order to save solvent, the same medium may be used for the washing according to process step (b) and for the hydrolysis/cyclisation according to process step (c), advantageously. For example, the washing can be carried out with acetic acid and thereafter the hydrolysis/cyclisation with HCl/acetic acid. It has proved to be necessary to use at least 2 equivalents of acid per g-atom of phosphorous bound in the polymer intermediate product in the acidic medium. For example, the acidic medium for this process step may be a dilute aqueous mineral acid. In such case, the thiophene derivative of general formula (I) formed stays absorbed on the anion exchange resin because of its non-solubility in water, and may be eluted from the resin by means of dilute alkaline brine after having been washed with water. In case acetic acid or a lower alkanol are used as solvents for the mineral acid or the strong organic acid, the thiophene compound of general formula (I) formed is present in dissolved form, and may be separated from the anion exchange resin by washing, e.g. with the same solvent.

The reaction of the purified polymer intermediate product of formula (III) with the acidic medium is generally carried out at temperatures from $+10°$ C. to $+60°$ C. The reaction time generally is 1 to 20, preferably 3 to 8 hours. The reaction is terminated, when 95 to 99 mol percent of the new polymer intermediate product of formula (III) have reacted chemically.

As is apparent from the above description of the process, the process of the invention has remarkable advantages, as compared to known processes for the preparation of the thiophene derivatives of general formula (I). In particular, the process of the invention is not subject to previous technical and apparative limitations. It makes the use of large amounts of solvent superfluous, requires only one crystallization up to the desired end product of formula (I), where previously four and more were necessary. The evaporation of the used solvent for recovery takes place without contact with the intermediate product of formula (III) and thus can be carried out under very economical conditions. Hence, the process of the invention provides a new advantageous synthesis of the thiophene derivatives of formula (I), leading to new polymer intermediate products of formula (III).

The invention is further explained by the following examples.

EXAMPLE 1

(A1)

Preparation of 1,3-diacetyl-4-bromomethyl-5-(5-ethoxycarbonylpentanoyl)-4-imidazol-2-one The compound of formula (V)

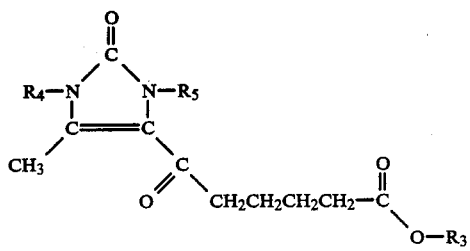

with $R_4=R_5=CH_3CO-$ and $R_3=C_2H_5$ [1,3-diacetyl-4-methyl-5-(5-ethoxycarbonylpentanoyl)-4-imidazol-2-one ($C_{16}H_{22}O_6N_2$), molecular weight 338.36], which was needed as a starting product, was prepared according to the teaching of R. Duschinsky and L. A. Dolan, "Am. Soc." 67 (1945), p. 2079–2084:

100 g (0.295 mol) 1,3-diacetyl-4-methyl-5-(5-ethoxycarbonylpentanoyl)-4-imidazol-2-one were dissolved in 1 l $CCl_4$ dried over $P_4O_{10}$ with stirring, and subsequently 52.5 g (0.295 mol) N-bromosuccinimide and 3 g succinimide were added. The mixture was heated and at the beginning of boiling 100 mg each of benzoylperoxide and azoisobutyronitrile were added. Now the start of the reaction—perceptible from the rising of the formed succinimide to the surface of the liquid—was waited for. After 2 hours the same amount benzoyl peroxide and azoisobutyronitrile was added again. After a reaction time of 4 hours bromination was completed. The mixture was cooled and the formed succinimide filtered and washed with 200 ml $CCl_4$. The filtrate was evaporated at 20° C. in a water-jet vacuum to an oily sirup. The crude halogenation product weighed 170 g and contained 113 g=0.271 mol (yield 92 mol percent) 1,3-diacetyl-4-bromomethyl-5-(5-ethoxy-carbonylpentanoyl)-4-imidazol-2-one ($C_{16}H_{21}BrO_6N_2$) (molecular weight 417.26), 7 g succinimide, 10 g unknown substances, the rest up to 170 g being $CCl_4$.

(A2)

The strong basic macroporous anion exchange resin to be used had the trade name "Amberlyst A 26". (Amberlyst ® is a trade mark of Rohm & Haas Co.). It contains the functional group $-CH_2-N^+(CH_3)_3$ and is in the chloride form.

In an ion exchange column having an inner diameter of 4 cm a resin bed 25 cm high was prepared with "Amberlyst A 26" from a suspension in water. Through this resin bed 80 g sodium monothiophosphate, $Na_3PO_3S.12H_2O$ (0.202 mol), dissolved in 2 l of water, were passed from the top to the bottom.

The resin column was washed with water, until salt free, and the water was replaced by dioxane. An elemental analysis of the ion exchanger gave a P:S:Cl ratio of 1:0.93:0.04 (on a g-atom to g-atom basis). The anion exchange mass "A" thus obtained showed no signs of decomposition over an observation period of 3 weeks.

50 g of the crude 1,3-diacetyl-4-bromomethyl-5-(5-ethoxycarbonylpentanoyl)-4-imidazol-2-one prepared above (corresponding to 0.079 g-atom bromine) were dissolved in a mixture of 5 ml dioxane and 50 ml dimethylformamide. The solution was agitated with 320 ml of the anion exchange mass "A" (containing 0.08 g-atom sulfur) over 96 hours at 20° C.

(B)

Thereafter, the mixture was poured onto a suction filter and the new polymer intermediate product washed 2 times with 400 ml dioxane each to remove by-products. Subsequently the resin mass was washed twice with 600 ml of methanol.

An elemental analysis of the new polymer intermediate products gave a S:Br ratio (g-atom to g-atom) of 1:0.94. Accordingly, 94 mol percent of the starting 1,3-diacetyl-4-bromomethyl-5-(5-ethoxy-carbonylpentanoyl)-4-imidazol-2-one had reacted with the monothiophosphate. The new polymer intermediate product had the morphology of the starting anion exchange resin and had the formula

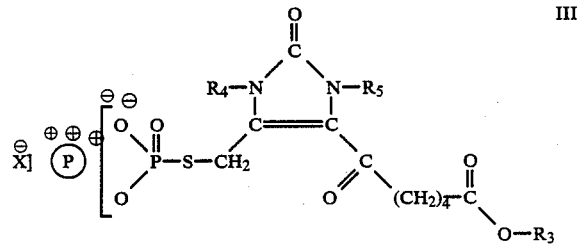

wherein $X=Br$, $R_4$ and $R_5=CH_3CO-$ and $R_3=C_2H_5$.

(C)

The washed polymer intermediate product from the preceding reaction step, still being wet from methanol, was then agitated with a solution of 21 g 31 percent hydrochloric acid (0.175 mol) and 19 g toluenesulfonic acid-monohydrate (0.1 mol) in 500 ml methanol over 8 hours at 58° C. to 60° C. Then the solution of the formed thiophene derivatives in methanol was separated from the anion exchange resin, which now is free of sulphur, on a pressurized suction filter. The resin bed was washed again with 1 l methanol and the combined filtrates (about 1.4 l) evaporated in vacuo. The evaporated residue was adjusted to pH 6 with 200 ml of an 0.1N solution of potassium phosphate and yielded 16.3 g (0.064 mol) 2,3,8,9-tetrahydrobiotin methyl ester of the formula

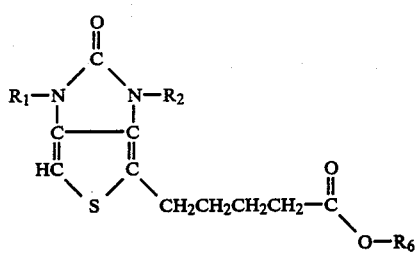

wherein $R_1=R_2=H$ and $R_6=CH_3$—; $C_{11}H_{14}N_2O_3S$; molecular weight 254.30, mp. 142° C. (yield 80 mol percent, based on the crude starting bromination product).

The anion exchange resin used was regenerated by washing with 1N caustic soda solution, rinsing with water and passing through of 0.1N hydrochloric acid.

EXAMPLE 2

(A)

The material used as anion exchange resin had the trade name "DOWEX MSA-1". (DOWEX ® is a trade mark of DOW CHEMICAL Co.). The resin is in the form of opaque balls having an average ball diameter of 0.3 to 1.2 mm. It is a strong basic anion exchanger with a macroporous structure. The functional group was methylene trimethyl ammonium, the counter ion upon delivery was the chloride.

300 ml of this resin, which was wet from water, were charged into the ion exchange column of example 1. The resin was converted to the acetate form by washing with 1 l of 1N sodium acetate solution. After rinsing with water, a solution of 80 g sodium monothiophosphate $Na_3PO_3S.12H_2O$ (0.202 mol) in 2 l water was passed through this resin bed from the top to the bottom.

The resin column was washed with water, until salt free, and the water was replaced by isopropanol. An elemental analysis of the ion exchanger gave a P:S:Cl ratio (g-atom to g-atom) of 1:0.98:0.01. The total resin column, which was wet from alcohol, contained 0.08 g-atom sulfur bonded as monothiophosphate and was transferred completely into an agitating vessel.

50 g of the crude bromination product 1,3-diacetyl-4-bromomethyl-5-(5-ethoxy-carbonylpentanoyl)-4-imidazol-2-one prepared in example 1 (corresponding to 0.079 g-atom bromine) were dissolved in a mixture of 300 ml each isopropanol and acetonitrile and agitated with the anion exchanger resin in the monothiophosphate form 60 hours at 30° C.

(B)

Thereafter, the mixture was transferred to a suction filter and the obtained new polymer intermediate product was washed 3 times with each 400 ml acetic acid to remove the by-products. The washed resin mass represented the new polymer intermediate product. An elemental analysis of the resin gave a S:Br ratio (g-atom to g-atom) of 1:0.96. Accordingly, 96 mol percent of the starting 1,3-diacetyl-4-bromomethyl-5-(5-ethoxy-carbonylpentanoyl)-4-imidazol-2-on had reacted with the monothiophosphate.

(C)

The new polymer intermediate product suspended in acetic acid was transferred back to the agitating vessel and agitated with a solution of 15 g anhydrous hydrochloric acid (0.4 mol in 500 ml glacial acetic acid for 8 hours at 28° C.).

Thereafter, the solution of the formed thiophene derivative in acetic acid was separated from the anion exchange resin, which is now sulfur free, on a pressurized suction filter. The resin bed was rewashed with 1 l glacial acetic acid and the combined filtrates (about 1.6 l) evaporated in vacuo after addition of 32 g anhydrous sodium acetate. The evaporated residue was triturated with 200 ml of ice water, adjusted to pH 2 with hydrochloric acid, the resulting precipitate was filtered and recrystallized from methanol. Thus, 14.4 g (0.060 mol) 2,3,8,9-tetrahydrobiotin of formula I were obtained:

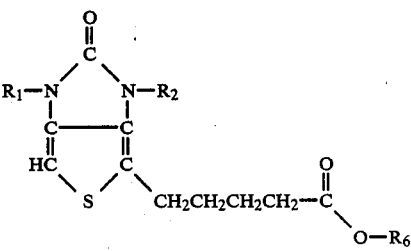

wherein $R_1=R_2=R_6=H$; $C_{10}H_{12}N_2O_3S$; molecular weight 240.28; mp. 240° C. (corresponding to a yield of 75 mol percent, based on the crude starting bromination product).

I claim:

1. A process for preparing thiophene derivatives of the general formula

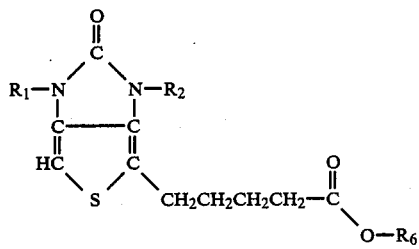

wherein $R_1$ and $R_2$, which may be the same or different, are each hydrogen or lower acyl, and $R_6$ is hydrogen or lower alkyl, characterized by (a) reacting a compound of the general formula

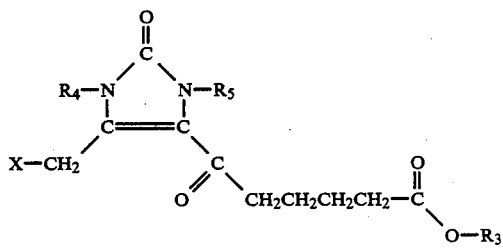

wherein $R_3$ is lower alkyl, $R_4$ and $R_5$ are lower acyl and X is chlorine, bromine or iodine, with a strong basic quaternary ammonium anion exchange resin in the monothiophosphate form to form a polymer compound of the general formula

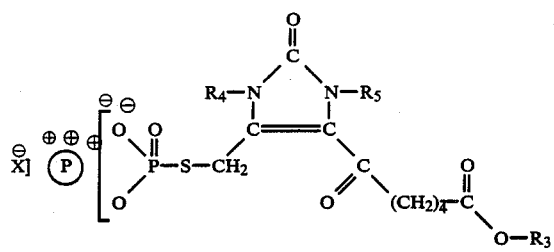

wherein $R_3$, $R_4$ and $R_5$ have the above significance and $(P)^{+++}$ represents a polymer cation, (b) separating the polymer intermediate product of formula (III) obtained in step (a) from non-reacted accompanying substances by washing with a washing liquid capable of dissolving the accompanying substances, and then (c) reacting the washed polymer intermediate product of formula (III) in an acidic medium to form the thiophene derivative of formula (I).

2. The process of claim 1, characterized in that an anion exchange resin having a macroporous structure and a polystyrene skeleton crosslinked with divinyl benzene is used in step (a), in which the quaternary ammonium groups are bonded to the carrier by means of a divalent residue.

3. The process of claim 1, characterized in that the reaction in step (a) is carried out at a temperature of $-10°$ to $+30°$ C. for a reaction time of 10 to 200 hours.

4. The process of claim 1, characterized in that the reaction in step (c) is carried out at temperatures of $+10°$ to $+60°$ C. for 1 to 20 hours.

* * * * *